United States Patent
Slowey et al.

(10) Patent No.: US 12,220,525 B2
(45) Date of Patent: Feb. 11, 2025

(54) TIOTROPIUM FORMULATION AND INHALER

(71) Applicant: KINDEVA DRUG DELIVERY L.P., St. Paul, MN (US)

(72) Inventors: Alexander D. Slowey, Bracknell (GB); Philip M. Cocks, Bracknell (GB); Neha A. Patel, Bracknell (GB)

(73) Assignee: Kindeva Drug Deliver L.P., Woodbury, MN (US)

( * ) Notice: Subject to any disclaimer, the term of this patent is extended or adjusted under 35 U.S.C. 154(b) by 809 days.

(21) Appl. No.: 16/973,863

(22) PCT Filed: Jun. 26, 2019

(86) PCT No.: PCT/US2019/039133
§ 371 (c)(1),
(2) Date: Dec. 10, 2020

(87) PCT Pub. No.: WO2020/006017
PCT Pub. Date: Jan. 2, 2020

(65) Prior Publication Data
US 2021/0260310 A1 Aug. 26, 2021

Related U.S. Application Data

(60) Provisional application No. 62/690,677, filed on Jun. 27, 2018.

(51) Int. Cl.
*A61M 15/00* (2006.01)
*A61K 9/00* (2006.01)
(Continued)

(52) U.S. Cl.
CPC ......... *A61M 15/0066* (2014.02); *A61K 9/008* (2013.01); *A61K 31/5386* (2013.01);
(Continued)

(58) Field of Classification Search
CPC ............ A61M 15/0066; A61M 15/009; A61M 2205/02; A61M 2207/00; A61K 9/008;
(Continued)

(56) References Cited

U.S. PATENT DOCUMENTS

| 8,414,956 B2 | 4/2013 | Jinks et al. |
| 8,479,732 B2 | 7/2013 | Stuart et al. |
(Continued)

FOREIGN PATENT DOCUMENTS

| WO | 2012173921 | 12/2012 |
| WO | 2017075018 | 5/2017 |

OTHER PUBLICATIONS

International Search Report and Written Opinion for PCT/US2019/039133 issued by the United States Patent and Trademark Office, Sep. 11, 2019; 9 pgs.
(Continued)

*Primary Examiner* — Joshua Lee
(74) *Attorney, Agent, or Firm* — Mueting Raasch Group

(57) ABSTRACT

A metered dose inhaler equipped with a metering valve and having an aerosol canister containing a pharmaceutical composition comprising propellant, ethanol, citric acid, and tiotropium or a pharmaceutically acceptable salt or solvate thereof dissolved in the composition, wherein the aerosol canister has an internal surface that is a non-metal material that is in contact with the pharmaceutical composition.

19 Claims, 4 Drawing Sheets

(51) Int. Cl.
*A61K 31/5386* (2006.01)
*A61K 47/10* (2017.01)
*A61K 47/12* (2006.01)
*A61K 47/24* (2006.01)

(52) U.S. Cl.
CPC .............. *A61K 47/10* (2013.01); *A61K 47/12* (2013.01); *A61K 47/24* (2013.01); *A61M 15/009* (2013.01); *A61M 2205/02* (2013.01)

(58) Field of Classification Search
CPC .. A61K 31/439; A61K 31/5386; A61K 47/10; A61K 47/12; A61K 47/24
See application file for complete search history.

(56) References Cited

U.S. PATENT DOCUMENTS

| | | | |
|---|---|---|---|
| 8,740,014 B2 | 6/2014 | Purkins et al. | |
| 8,814,035 B2 | 8/2014 | Stuart | |
| 8,815,325 B2 | 8/2014 | David et al. | |
| 9,364,540 B2* | 6/2016 | Dalvi | A61K 9/007 |
| 9,655,969 B2 | 5/2017 | Zeng | |
| 9,707,295 B2* | 7/2017 | Dalvi | A61K 9/08 |
| 10,034,866 B2 | 7/2018 | Zeng | |
| 10,364,256 B2* | 7/2019 | Callahan | C07D 401/12 |
| 2005/0058606 A1* | 3/2005 | Six | A61K 47/02 |
| | | | 424/46 |
| 2007/0128123 A1* | 6/2007 | Six | A61K 47/12 |
| | | | 424/45 |
| 2009/0175802 A1* | 7/2009 | Six | A61K 31/439 |
| | | | 128/200.23 |
| 2010/0247932 A1 | 9/2010 | Jinks et al. | |
| 2012/0097159 A1 | 4/2012 | Iyer et al. | |
| 2012/0234317 A1 | 9/2012 | Stuart | |
| 2013/0302260 A1* | 11/2013 | Berner | A61K 9/0078 |
| | | | 128/200.14 |
| 2014/0348758 A1 | 11/2014 | Zeng | |
| 2014/0373832 A1 | 12/2014 | Zeng et al. | |
| 2015/0190510 A1* | 7/2015 | Dalvi | A61K 47/12 |
| | | | 128/200.14 |
| 2015/0258024 A1* | 9/2015 | Berner | A61K 31/46 |
| | | | 128/200.23 |
| 2016/0106664 A1* | 4/2016 | Berner | A61P 11/00 |
| | | | 424/45 |
| 2016/0243241 A1* | 8/2016 | Dalvi | A61M 15/0021 |
| 2016/0250197 A1* | 9/2016 | Dalvi | A61M 11/00 |
| | | | 424/45 |
| 2017/0020852 A1 | 1/2017 | Zeng | |
| 2017/0367971 A1* | 12/2017 | Berner | A61K 47/12 |
| 2018/0282349 A1* | 10/2018 | Callahan | A61K 9/0019 |
| 2019/0054010 A1* | 2/2019 | Slowey | A61K 47/10 |
| 2019/0161480 A1* | 5/2019 | Campos | A61P 11/06 |

OTHER PUBLICATIONS

International Preliminary Report on Patentability for PCT/US2019/039133 issued by the United States Patent and Trademark Office; Dec. 29, 2020; 5 pgs.
Extended European Search Report for EP Application No. 19824940.1 issued by the European Patent Office on Feb. 24, 2022; 8 pgs.

* cited by examiner

TIOTROPIUM FORMULATION AND INHALER

This application is the § 371 U.S. National Stage of International Application No. PCT/US2019/039133, filed 26 Jun. 2019, which claims the benefit of U.S. Provisional Application No. 62/690,677, filed 27 Jun. 2018, each of which is incorporated by reference herein in its entirety.

FIELD

The present disclosure generally relates to formulations used for, as an example, inhaled dosage forms, as well as aerosol canisters, inhalers, such as metered dose inhalers, containing the same. In particular, the present disclosure relates to formulations including tiotropium.

BACKGROUND

Tiotropium compositions are known in the art. Such compositions are not necessarily acceptable, for example, such compositions may not be acceptable for use in inhalers. Further, such formulations are not necessarily solution formulations.

SUMMARY

It has been discovered that a stable, pharmaceutically acceptable metered dose inhaler having an aerosol container can comprise a pharmaceutical composition comprising propellant, ethanol, citric acid, and tiotropium or a pharmaceutically acceptable salt or solvate thereof dissolved in the composition, wherein the aerosol canister has an internal surface that is a non-metal material that is in contact with the pharmaceutical composition. In particular, the tiotropium may be in the form of tiotropium bromide and the propellant may consist essentially of HFA-134a (1,1,1,2-tetrafluoroethane). The concentration of the tiotropium may be between about 0.07 mg/mL and 0.15 mg/mL and the concentration of citric acid may be between about 0.02 wt. % and 0.15 wt. %. More preferably, the concentration of the citric acid may be about 0.04 wt. %.

The non-metal material can beneficially comprise a silane primer composition having two or more reactive silane groups separated by an organic linker group disposed thereon, wherein the silane primer composition has a coating composition comprising an at least partially fluorinated compound disposed thereon. In particular, the non-metal material can comprise a polyfluoropolyether silane, such as fluorinated ethylene propylene (FEP) copolymer, in order to help provide stability.

DETAILED DESCRIPTION

Figure 1:
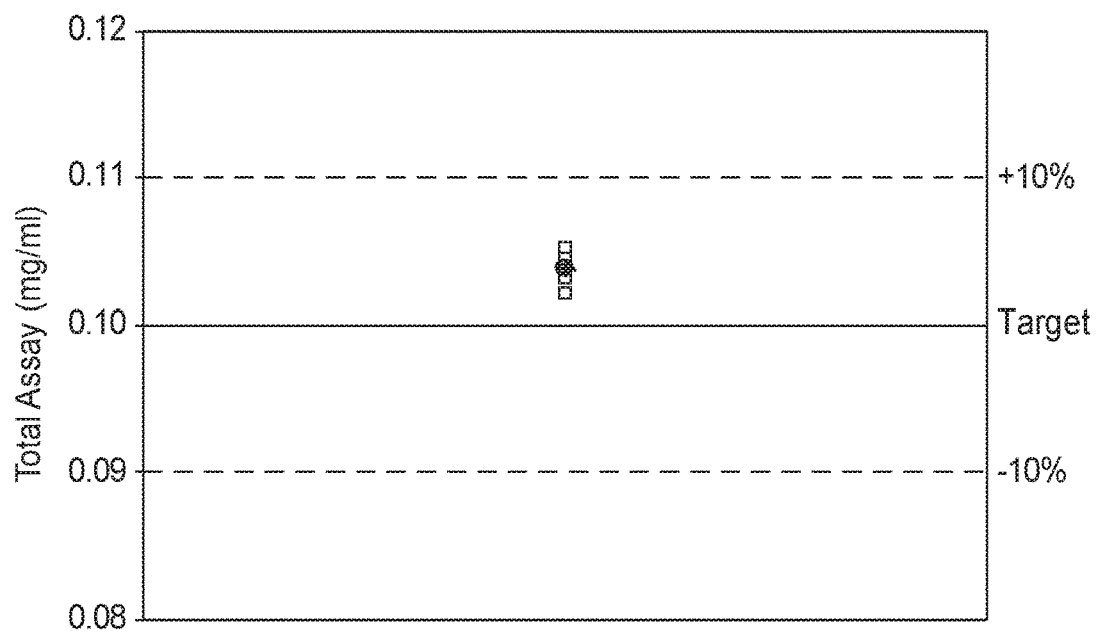
FIG. 1 is a plot of the uniformity of the total tiotropium content for an example formulation.
Figure 2:
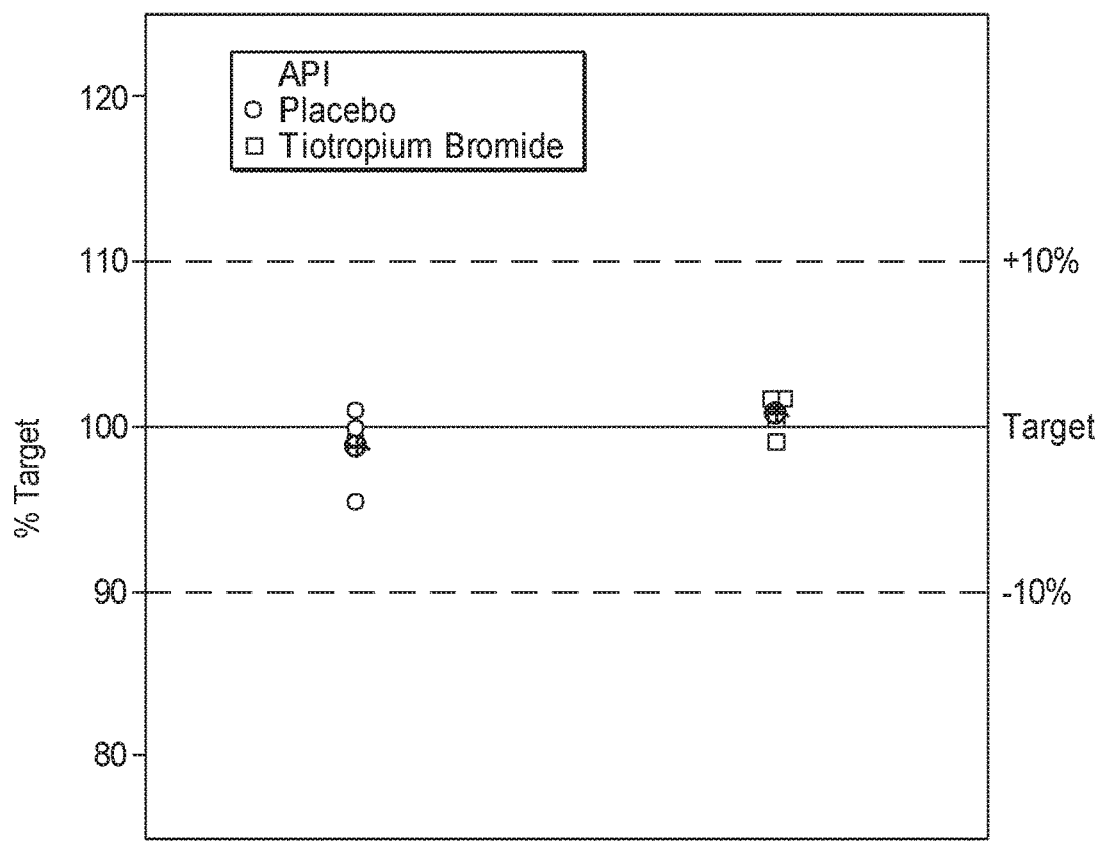
FIG. 2 is a plot of the uniformity of the citric acid content for an example formulation.
Figure 3:
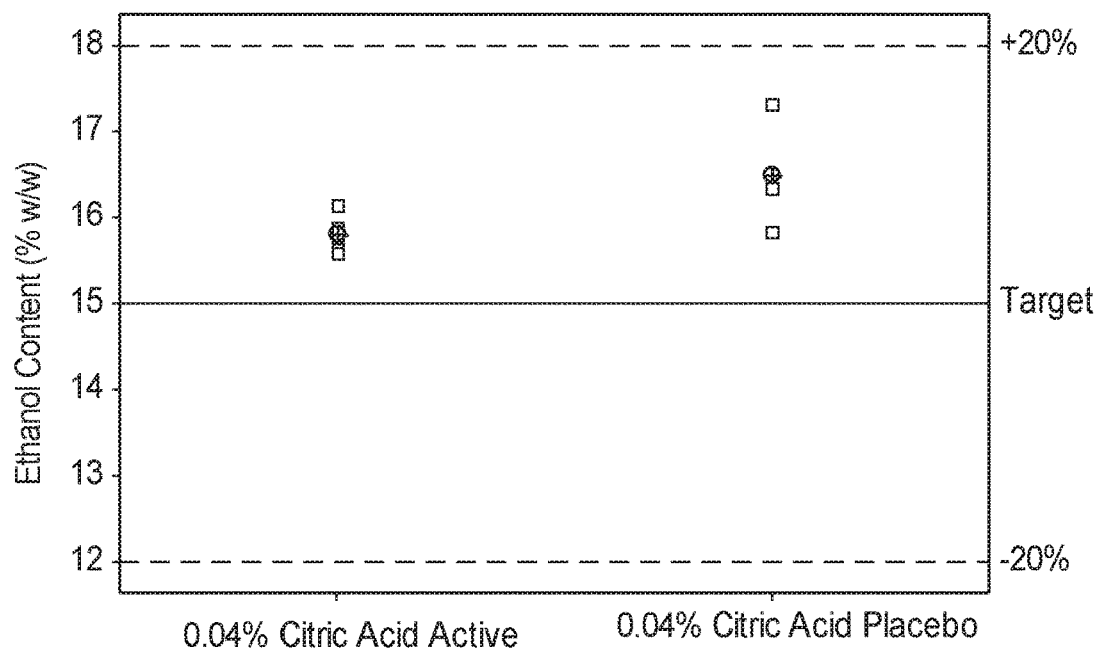
FIG. 3 is a plot of the uniformity of the ethanol content for an example formulation.

Throughout this disclosure, singular forms such as "a," "an," and "the" are often used for convenience; however, it should be understood that the singular forms are meant to include the plural unless the singular alone is explicitly specified or is clearly indicated by the context.

Some terms used in this application have special meanings, as defined herein. All other terms will be known to the skilled artisan, and are to be afforded the meaning that a person of skill in the art at the time of the invention would have given them.

Elements in this specification that are referred to as "common," "commonly used," and the like, should be understood to be common within the context of the compositions, articles, such as inhalers and metered dose inhalers, and methods of this disclosure; this terminology is not used to mean that these features are present, much less common, in the prior art. Unless otherwise specified, only the Background section of this Application refers to the prior art.

The "particle size" of a single particle is the size of the smallest hypothetical hollow sphere that could encapsulate the particle.

The "mass median diameter" of a plurality of particles refers to the value for a particle diameter at which 50% of the mass of particles in the plurality of particles have a particle size smaller than the value and 50% of the mass of particles in the plurality of particle have a particle size greater than the value.

The "ex-actuator size" of a plurality of particles refers to the mass median aerodynamic diameter (sometimes abbreviated as "MMAD") of the plurality of particles after the plurality of particles has passed through the actuator of an inhaler, such as a metered dose inhaler, as measured by the procedure described in the United States Pharmacopeia <601>.

"Weight percent" or "percent by weight," when describing the amount of component in a composition refers to percent weight of the component based on the weight of the entire composition.

Weight percent is sometimes abbreviated "wt. %."

"Fine particle dose" is determined according to 2015 United States Pharmacopia test <601>.

"Fine Particle Mass," often abbreviated "FPM," is in this disclosure determined mathematically using Copley Inhaler Testing Data Analysis Software (CITDAS) (Copley Scientific LTD., Nottingham, United Kingdom).

"Fine Particle Fraction," often abbreviated "FPF," is determined according to 2015 United States Pharmacopia test <601> and is calculated as [FPM/(sum of sample content for throat assembly, cups 1-7, MOC, and the filter)]× 100.

A component is said to be present in amounts "up to" a reference amount or concentration when the component is not absent but is present in an amount no greater than the reference amount or concentration. Thus, a component present "up to" an amount or concentration does not include the case where the component is absent or present in 0% concentration.

When the concentration of tiotropium is discussed in this disclosure, for convenience it is referred to in terms of the concentration of tiotropium bromide, unless the disclosure specifically refers to the salt form. It should therefore be understood that if another form or salt of tiotropium is used, the concentration of that other form or salt should be calculated on a basis relative to tiotropium bromide.

A person of ordinary skill in the relevant arts can easily perform this calculation by comparing the molecular weight of the form or salt of tiotropium that is used to the molecular weight of tiotropium bromide.

Formulation

The formulation can be a solution. Solution formulations, especially for use in aerosols, can have several advantages over suspension formulations. Such advantages include being homogeneous so that users do not need to agitate the formulation to ensure a correct dose. Also, because they are homogeneous, solution formulations provide essentially identical amounts of drug per mass of dose for each dose in an inhaler, whereas inhomogeneous suspensions may lack this consistency. However, it is often a challenge to achieve a solution formulation with acceptable chemical and physical stability and having good delivery characteristics.

The pharmaceutical formulation comprises tiotropium. Tiotropium is a cationic material, and is therefore typically in the form of one or more physiologically acceptable salts or solvates. Tiotropium bromide is most common. In some cases, the tiotropium bromide is anhydrous tiotropium bromide. Any suitable concentration of tiotropium can be used. When the concentration of tiotropium is expressed in terms of mg/mL of tiotropium bromide, then the concentration of tiotropium may preferably be no more than 0.15 mg/ml, no more than 0.14 mg/ml, no more than 0.13 mg/ml, no more than 0.12 mg/ml, no more than 0.11 mg/ml, no more than 0.10 mg/ml, no more than 0.09 mg/ml, no more than 0.08 mg/ml, no more than 0.07 mg/ml, no more than 0.06 mg/ml, or no more than 0.05 mg/ml. The concentration of tiotropium, again expressed in terms of tiotropium bromide, may preferably be no less than 0.05 mg/ml, no less than 0.06 mg/ml, no less than 0.07 mg/ml, no less than 0.08 mg/ml, no less than 0.09, no less than 0.1 mg/ml, no less than 0.11 mg/ml, no less than 0.12 mg/ml, or no less than 0.13 mg/ml. Particular embodiments use tiotropium in an amount of about 0.08 mg/ml to about 0.12 mg/ml, such as 0.08 mg/ml to 0.12 mg/ml, about 0.09 mg/ml to about 0.11 mg/ml, such as 0.09 mg/ml to 0.11 mg/ml, about 0.1 mg/ml, or in some cases 0.1 mg/ml. When the tiotropium is in the form of tiotropium bromide, 0.1 mg/ml corresponds to 0.1204 mg/ml tiotropium bromide. When expressed in terms of wt. %, the concentration of tiotropium (in terms of tiotropium bromide) is often no greater than 0.015, no greater than 0.014, no greater than 0.0125, or no greater than 0.012. When expressed in terms of wt. %, the concentration of tiotropium (in terms of tiotropium bromide) is often no less than 0.005, no less than 0.006, no less than 0.0075, no less than 0.008, or no less than 0.01.

The ex-actuator size of the tiotropium particles, such as tiotropium bromide particles, can be any suitable ex-actuator size. Exemplary suitable ex-actuator sizes may be no less than 1 micrometer no less than 1.5 micrometers, no less than 2 micrometers, no less than 2.5 micrometers, no less than 3 micrometers, or no less than 3.5 micrometers. Exemplary suitable ex-actuator sizes may also be no greater than 5.0 micrometers, no greater than 4.5 micrometers, no greater than 4.0 micrometers, no greater than 3.5 micrometers, no greater than 3.0 micrometers, no greater than 2.5 micrometers, no greater than 2.0 micrometers, or no greater than 1.5 micrometers. 2.5 micrometer to 3.5 micrometers is common.

The tiotropium particles, such as tiotropium bromide particles, produced by the inhaler can also be characterized by the mass of their fine particle dose. The mass of the fine particle dose, in micrograms, is typically no more than 4, no more than 3.5, no more than 3, no more than 2, such as no more than 1.9, no more than 1.8, no more than 1.7, no more than 1.6, or no more than 1.5. The mass of the fine particle dose is also typically no less than 0.5, such as no less than 0.6, no less than 0.7, or no less than 0.8.

As noted, the tiotropium can be present in any suitable concentration in the formulation and the concentration is often expressed in terms of tiotropium bromide; if a different tiotropium salt is used, a person of ordinary skill in the art is able to calculate the concentration of the particular tiotropium salt used in terms of tiotropium bromide using the ratio of the molar mass of the tiotropium salt being used to the molar mass of tiotropium bromide.

One or more stabilizing agents can be included. The one or more stabilizing agents can be any agent that increases the stability of the formulation. The stabilizing agents can be, for example, antioxidants such as sacrificial antioxidants. Any pharmaceutically acceptable stabilizing agent can be used. An organic acid is an example of such stabilizing agent that can be included in the composition. The organic acid can be ascorbic acid, fumaric acid, or citric acid. One particular stabilizing agent is citric acid or a salt thereof. When citric acid is used, preferable initial concentrations of citric acid can be no less than 0.01 wt. %, no less than 0.02 wt. %, no less than 0.03 wt. %, no less than, no less than 0.04 wt., no greater than 0.15 wt. %, no greater than 0.1 wt. %, no greater than 0.09 wt. %, no greater than 0.08 wt. %, no greater than 0.07 wt. %, no greater than 0.06 wt. %, no greater than 0.05 wt. %, no greater than 0.04 wt. %, between 0.01 and 0.15 wt. %, between 0.02 and 0.1 wt. %, or between 0.03 and 0.05 wt. %. An exemplary initial citric acid concentration includes 0.04 wt. %, wherein there is enough citric acid present in the composition to stabilize the tiotropium without significant formation of impurities that are observed at higher concentrations of citric acid. The concentration of citric acid can decrease over the shelf life of the composition. When a salt of citric acid is used, the weight percent values in this paragraph should be understood to be based on the weight of free citric acid (i.e., without considering the weight of the cation). Most commonly, citric acid alone is used.

A propellant is also included in the formulation. The prior art recognizes two common propellants for MDI aerosol formulations: HFA-134a and HFA-227. Another non-CFC propellant that can be used, for example, is HFA-152a. In the prior art, HFA-134a and HFA-227 are often deemed to be equivalent. Surprisingly, however, for the specific formulations disclosed in this application, solutions cannot be formed if the propellant is HFA-227. In order to form solutions, the propellant must consist essentially of HFA-134a (also known as 1,1,2-tetrafluoroethane). In this context, "consisting essentially of" means that there is sufficient HFA-134a to create a solution formulation; minor, insubstantial, or trace amounts of other propellants, such as HFA-227, can be present so long as those amounts are insufficient to cause the components to either not form a solution or to cause one or more components of the solution to precipitate after the solution is formed. The inventors prepared several tiotropium compositions that are analogous to those described herein but using HFA-227 instead of HFA-134a, and none of the HFA-227 compositions formed solutions that were stable upon storage; most HFA-227 compositions did not form solutions at all. Thus, the HFA-134a content of the propellant on a weight percent basis is typically at least 90%, such as at least 91%, at least 92%, at least 93%, at least 94%, at least 95%, at least 96%, at least 97% at least 98%, at least 99%, at least 99.25%, at least 99.5%, or at least 99.75%. In some cases the propellant comprises substantially only 1,1,1,2-tetrafluoroethane.

On a weight percent basis, the amount of propellant in the formulation is typically at least 78% or at least 83%. In many cases, the propellant is 80 to 85 percent by weight, or 83 to 85 percent by weight of the formulation.

An organic alcohol is also included in the composition. The organic alcohol can be methanol, ethanol, propanol, butanol, or other alcohols known in the art. Preferably the organic alcohol is ethanol. Ethanol is used to ensure adequate concentration of drug can be dissolved in the propellant system. On a weight percent basis, the amount of ethanol used, if any, is typically no greater than 20, no greater than 19, no greater than 18, no greater than 17 no greater than 16, no greater than 15.5, no greater than 15, no greater than 14.5, no greater than 13, no greater than 12, no greater than 11, or no greater than 10. The amount of ethanol used can also be, on a weight percent basis, no less than 10, no less than 11, no less than 12, no less than 13, no less than 14, no less than 14.5, no less than 15, no less than 15.5, no less than 16, no less than 17 or no less than 18. In many cases, the ethanol is about 13 to about 17 percent by weight, 13 to 17 percent by weight, such as about 14 to about 16 percent by weight, 14 to 16 percent by weight, about 14.5 to about 15.5 percent by weight, 14.5 to 15.5 percent by weight, or, in one particular case, about 15 percent by weight or more particularly 15 percent by weight. Even with the addition of ethanol a solution of adequate concentration of tiotropium has not been made with HFA-227 as the propellant. Formulations that were attempted with large amounts of HF-227 propellant did not form solutions.

In many cases, the combined amount of propellant and ethanol in the formulation, on a weight percent basis, is at least 95 percent, at least 97 percent, at least 98 percent, at least 99 percent, at least 99.5 percent, or at least 99.7 percent.

One or more ex-actuator size affecting compound can be included. Ex-actuator size affecting compounds can change the size of the drug particles as measured after actuation of an inhaler, such as a metered dose inhaler, containing the composition. Surfactants can be used for this purpose. Most pharmaceutically acceptable surfactants are suitable for use with an inhaler. Typical surfactants include oleic acid, sorbitan monooleate, sorbitan trioleate, soya lecithin, polyethylene glycol, polyvinylpyrrolidone, or combinations thereof. Oleic acid, polyvinylpyrrolidone, or a combination thereof is most common. A combination of polyvinylpyrrolidone and polyethylene glycol is also commonly employed. When polyvinylpyrrolidone is employed, it can have any suitable molecular weight. Examples of suitable weight average molecular weights are from 10 to 100 kilodaltons, typically from 10 to 50, 10 to 40, 10 to 30 or 10 to 20 kilodaltons. When polyethylene glycol is employed, it can be any suitable grade. PEG 100 and PEG 300 are most commonly employed. Most commonly, however, the ex-actuator size affecting compound is glycerol. Alternatively, the one or more ex-actuator size affecting compound may excluded.

When used, an ex-actuator size affecting compound, particularly glycerol, can be present in a weight percent basis of no more than 2.0%, no more than 1.9%, no more than 1.8%, no more than 1.7%, no more than 1.6%, no more than 1.55%, no more than 1.5%, no more than 1.45%, no more than 1.4%, no more than 1.3%, no more than 1.2%, no more than 1.1%, no more than 1.0%, no more than 0.9%, no more than 0.8%, or no more than 0.75%. The ex-actuator size affecting compound, particularly glycerol, can be present in a weight percent basis of no less than 1.0%, no less than 1.1%, no less than 1.2%, no less than 1.3%, no less than 1.4%, no less than 1.45%, no less than 1.5%, no less than 1.55%, no less than 1.6%, no less than 1.7%, no less than 1.8%, or no less than 1.9%. Thus, the ex-actuator size affecting compound, particularly glycerol, can be present, on a weight percent basis, in about 0.7% to about 1.7%, 0.7% to 1.7%, about 0.8% to 1.6%, 0.8% to 1.6%, about 0.9% to about 1.6%, 0.9% to 1.6%, about 1.0% to about 1.5%, or 1.0% to 1.5%. Particular examples use either 1.0% or 1.5%.

The formulations as described herein can be particularly advantageous because they can stabilize the tiotropium, such as tiotropium bromide, contained therein. Stability of the formulation can be measured by analyzing change in fine particle fraction over time.

The above-described formulations can be used with metered dose inhalers known in the art.

Inhaler

Any of the above-described formulations can be used with any type of inhaler. Metered dose inhalers are most common. When the inhaler is a metered dose inhaler, any metered dose inhaler can be employed. Suitable metered dose inhalers are known in the art. A typical example, incorporated herein by reference, of a pressurized metered dose inhaler is shown in published PCT application WO 2012/173921.

For example, the above-described formulations can be present in a canister, such as a sealed canister.

Such sealed canister can contain any of the above-described formulations under pressure, particularly under a pressure greater than ambient atmospheric pressure.

Typical metered dose inhalers for the pharmaceutical formulations described herein contain an aerosol canister fitted with a valve. The canister can have any suitable volume. The brimful capacity canister will depend on the volume of the formulation that is used to fill the canister. In typical applications, the canister will have a volume from 5 mL to 50 mL, such as, for example 5 mL to 20 mL, 10 mL to 50 mL, 8 mL to 20 mL, or 8 mL to 15 mL. The canister will often have sufficient volume to contain enough medicament for delivering an appropriate number of doses. The appropriate number of doses is discussed herein. The valve is typically affixed, or crimpled, onto the canister by way of a cap or ferrule. The cap or ferrule is often made of aluminum or an aluminum alloy, which is typically part of the valve assembly. One or more seals can be located between the canister and the ferrule. The seals can be one or more of O-ring seals, gasket seals, and the like. The valve is typically a metered dose valve. Typical valve sizes range from 20 microliters to 100 microliters. Specific valve size that are commonly employed include 25, 50, 60, and 63 microliter valve sizes.

The container and valve typically include an actuator. Most actuators have a patient port, which is typically a mouthpiece, for delivering the formulation contained in the canister. The patient port can be configured in a variety of ways depending on the intended destination of the formulation. For example, a patient port designed for administration to the nasal cavities will generally have an upward slope to direct the formulation to the nose. The actuator is most commonly made out of a plastic material. Typical plastic materials for this purpose include at least one of polyethylene and polypropylene. Typical MDIs have an actuator with a nozzle. In use, the aerosol spray can emerge from this nozzle before exiting the mouthpiece of the actuator. The nozzle can be characterized by an orifice diameter and a jet length. Any suitable orifice diameter can be used. Typical orifice diameters are from 0.2 mm to 0.65 mm, with 0.2 mm to 0.4 mm being particularly useful for delivery of solution formulations, such as the solution formulations discussed herein. Typical orifice jet length is from 0.5 mm to 1 mm. Specific examples include orifice diameters of 0.25 mm, 0.3 mm, or 0.4 mm, any of which can have a jet length of 0.8 mm.

A metered dose valve is typically present, and is often located at least partially within the canister and at least partially in communication with the actuator. Typical metered dose valves include a metering chamber that is at least partially defined by an inner valve body through which a valve stem passes.

The valve stem can be biased outwardly by a compression spring to be in a sliding sealing engagement with an inner tank seal and outer diaphragm seal. The valve can also include a second valve body in the form of a bottle emptier. The inner valve body, which is sometimes referred to as the primary valve body, defines, in part, the metering chamber. The second valve body, which is sometimes referred to as the secondary valve body, defines, in part, a pre-metering region (sometimes called a pre-metering chamber) in addition to serving as a bottle emptier. The outer walls of the portion of the metered dose valve that are located within the canister, as well as the inner walls of the canister, define a formulation chamber for containing the pharmaceutical formulation.

In use, the pharmaceutical formulation can pass from the formulation chamber into the metering chamber. In moving to the metering chamber, the formulation can pass into the above-mentioned pre-metering chamber through an annular space between the secondary valve body (or a flange of the secondary valve body) and the primary valve body. Pressing the valve stem towards the interior of the container actuates the valve, which allows the pharmaceutical formulation to pass from the pre-metering chamber through a side hole in the valve stem, through an outlet in the valve stem, to an actuator nozzle, and finally through the patient port to the patient. When the valve stem is released, the pharmaceutical formulation enters the valve, typically to the pre-metering chamber, through an annular space and then travels to the metering chamber.

The pharmaceutical formulation can be placed into the canister by any known method. The two most common methods are cold filling and pressure filling. In a cold filling process, the pharmaceutical formulation is chilled to an appropriate temperature, which is typically −50° C. to −60° C. for formulations that use propellant HFA 134a, HFA 227, or a combination thereof, and added to the canister. The metered dose valve is subsequently crimped onto the canister. When the canister warms to ambient temperature, the vapor pressure associated with the pharmaceutical formulation increases thereby providing an appropriate pressure within the canister.

In a pressure filling method, the metered dose valve can be first crimped onto the empty canister. Subsequently, the formulation can be added through the valve into the container by way of applied pressure. Alternatively, all of the non-volatile components can be first added to the empty canister before crimping the valve onto the canister. The propellant can then be added through the valve into the canister by way of applied pressure.

The total dose of tiotropium, such as tiotropium bromide, that is delivered in a single actuation can be any suitable dose depending on the nature of the condition and patient population that the inhaler is designed to treat. Typically, the total dose delivered per actuation, in micrograms, is no less than 0.5, no less than 1, no less than 1.5, or no less than 3, such as no less than 3.25, no less than 3.75, no less than 4, or no less than 4.25. Typically, the total dose delivered per actuation, in micrograms, is no more than 7.5, no more than 7.25, no more than 7.0, no more than 6.5, no more than 6.25, no more than 6.0, no more than 5.75, no more than 5.5, no more than 5.25, no more than 5, no more than 4.75, no more than 4.0, no more than 3.5, no more than 3.0, or no more than 2.0. Commonly the dose is between 3 micrograms and 6 micrograms per actuation. More commonly the dose is between 4 micrograms and 5.5 micrograms per actuation. The dose is commonly about 5 micrograms per actuation.

Typical inhalers, such as metered dose inhalers, are designed to deliver a specified number of doses of the pharmaceutical formulation. A dose is sometimes deliverable by a single actuation of the inhaler, but can also be deliverable by two, three, four, or more actuations. In most cases, the specified number of doses is from 10 to 100, such as from 20-40. One commonly employed metered dose inhaler is designed to provide 30 doses whereby each dose is delivered in two actuations; this can be employed with any of the formulations or inhaler types described herein.

The inhaler, particularly when it is a metered dose inhaler, can contain a dose counter for counting the number of doses. Suitable dose counters are known in the art, and are described in, for example, U.S. Pat. Nos. 8,740,014, 8,479,732, U.S. Patent Application Publication No. 2012/0234317, and U.S. Pat. No. 8,814,035, all of which are incorporated by reference for their disclosures of dose counters. One exemplary dose counter, which is described in detail in U.S. Pat. No. 8,740,014 (which is hereby incorporated by reference for its disclosure of the dose counter) has a fixed ratchet element and a trigger element that is constructed and arranged to undergo reciprocal movement coordinated with the reciprocal movement between an actuation element in an inhaler and the dose counter. The reciprocal movement typically comprises an outward stroke (outward being with respect to the inhaler) and a return stroke. The return stroke returns the trigger element to the position that it was in prior to the outward stroke. A counter element is also included in this type of dose counter. The counter element is constructed and arranged to undergo a predetermined counting movement each time a dose is dispensed. The counter element is biased towards the fixed ratchet and trigger elements and is capable of counting motion in a direction that is substantially orthogonal to the direction of the reciprocal movement of the trigger element.

The counter element in the above-described dose counter comprises a first region for interacting with the trigger member. The first region comprises at least one inclined surface that is engaged by the trigger member during the outward stroke of the trigger member. This engagement during the outward stroke causes the counter element to undergo a counting motion. The counter element also comprises a second region for interacting with the ratchet member. The second region comprises at least one inclined surface that is engaged by the ratchet element during the return stroke of the trigger element causing the counter element to undergo a further counting motion, thereby completing a counting movement. The counter element is normally in the form of a counter ring, and is advanced partially on the outward stroke of the trigger element, and partially on the return stroke of the trigger element. As the outward stroke of the trigger typically corresponds to the depression of a valve stem that causes firing of the valve (and, in the case of a metered dose inhaler, also meters the contents) and the return stroke typically corresponds to the return of the valve stem to its resting position, this dose counter allows for precise counting of doses.

Another suitable dose counter, which is described in detail in U.S. Pat. No. 8,479,732 (which is incorporated by reference for its disclosure of dose counters) is specially adapted for use with a metered dose inhaler. This dose counter includes a first count indicator having a first indicia bearing surface. The first count indicator is rotatable about a first axis. The dose counter also includes a second count indicator having a second indicia bearing surface. The second count indicator is rotatable about a second axis. The first and second axes are disposed such that they form an obtuse angle. The obtuse angle mentioned above can be any obtuse angle, but is advantageously 125 to 145 degrees. The obtuse angle permits the first and second indicia bearing surface to align at a common viewing area to collectively present at least a portion of a medication dosage count. One or both of the first and second indicia bearing surfaces can be marked with digits, such that when viewed together through the viewing area the numbers provide a dose count. For example, one of the first and second indicia bearing surface may have "hundreds" and "tens" place digits, and the other with "ones" place digits, such that when read together the two indicia bearing surfaces provide a number between 000 and 999 that represents the dose count.

Yet another suitable dose counter is described in U.S. Patent Application Publication No. 2012/0234317 (hereby incorporated by reference for its disclosure of dose counters). Such a dose counter includes a counter element that undergoes a predetermined counting motion each time a dose is dispensed. The counting motion is typically vertical or essentially vertical. A count indicating element is also included. The count indicating element, which undergoes a predetermined count indicating motion each time a dose is dispensed, includes a first region that interacts with the counter element.

The counter element has regions for interacting with the count indicating element. Specifically, the counter element comprises a first region that interacts with a count indicating element. The first region includes at least one surface that it engaged with at least one surface of the first region of the aforementioned count indicating element. The first region of the counter element and the first surface of the count inducing element are disposed such that the count indicating member completes a count indicating motion in coordination with the counting motion of the counter element, during and induced by the movement of the counter element, the count inducing element undergoes a rotational or essentially rotational movement. In practice, the first region of the counter element or the counter indicating element can comprise, for example, one or more channels. A first region of the other element can comprise one or more protrusions adapted to engage with said one or more channels. Yet another dose counter is described in U.S. Pat. No. 8,814,035 (hereby incorporated by reference for its disclosure of dose counters). Such a dose counter is specially adapted for use with an inhaler with a reciprocal actuator operating along a first axis. The dose counter includes an indicator element that is rotatable about a second axis. The indicator element is adapted to undergo one or more predetermined count-indicating motions when one or more doses are dispensed. The second axis is at an obtuse angle with respect to the first axis. The dose counter also contains a worm rotatable about a worm axis. The worm is adapted to drive the indicator element. It may do this, for example, by containing a region that interacts with and enmeshes with a region of the indicator element. The worm axis and the second axis do not intersect and are not aligned in a perpendicular manner. The worm axis is also, in most cases, not disposed in coaxial alignment with the first axis. However, the first and second axes may intersect.

At least one of the various internal components of an inhaler, such as a metered dose inhaler, as described herein, such as one or more of the canister, valve, gaskets, seals, O-rings, and the like, can be coated with one or more coatings. Some of these coatings provide a low surface energy. Such coatings are not required because they are not necessary for the successful operation of all inhalers. Some coatings that can be used are described in U.S. Pat. Nos. 8,414,956, 8,815,325 and U.S. Patent Application Publication No. US2012/0097159, all of which are incorporated by reference for their disclosure of coatings for inhalers and inhaler components.

A first acceptable coating can be provided by the following method:
a) providing one or more component of the inhaler, such as the metered dose inhaler,
b) providing a primer composition comprising a silane having two or more reactive silane groups separated by an organic linker group,
c) providing a coating composition comprising an at least partially fluorinated compound,
d) applying the primer composition to at least a portion of the surface of the component,
e) applying the coating composition to the portion of the surface of the component after application of the primer composition.

The at least partially fluorinated compound will usually comprise one or more reactive functional groups, with the or each one reactive functional group usually being a reactive silane group, for example a hydrolysable silane group or a hydroxysilane group. Such reactive silane groups allow reaction of the partially fluorinated compound with one or more of the reactive silane groups of the primer. Often such reaction will be a condensation reaction.

One exemplary silane that can be used has the formula $$X_{3-m}(R_1)_m Si-Q-Si(R^2)_k X_{3-k}$$

wherein $R^1$ and $R^2$ are independently selected univalent groups, X is a hydrolysable or hydroxy group, m and k are independently 0, 1, or 2 and Q is a divalent organic linking group.

Useful examples of such silanes include one or a mixture of two or more of 1,2-bis(trialkoxysilyl) ethane, 1,6-bis(trialkoxysilyl) hexane, 1,8-bis(trialkoxysilyl) octane, 1,4-bis(trialkoxysilylethyl)benzene, bis(trialkoxysilyl)itaconate, and 4,4'-bis(trialkoxysilyl)-1,1'-diphenyl, wherein any trialkoxy group may be independently trimethoxy or triethoxy.

The coating solvent usually comprises an alcohol or a hydrofluoroether.

If the coating solvent is an alcohol, preferred alcohols are $C_1$ to $C_4$ alcohols, in particular, an alcohol selected from ethanol, n-propanol, or iso-propanol or a mixture of two or more of these alcohols. If the coating solvent is a hydrofluoroether, it is preferred that the coating solvent comprises a $C_4$ to $C_{10}$ hydrofluoroether. Generally, the hydrofluoroether will be of formula $$C_g F_{2g+1} O C_h H_{2h+i}$$

wherein g is 2, 3, 4, 5, or 6 and h is 1, 2, 3 or 4. Examples of suitable hydrofluoroethers include those selected from the group consisting of methyl heptafluoropropylether, ethyl heptafluoropropylether, methyl nonafluorobutylether, ethyl nonafluorobutylether and mixtures thereof.

The polyfluoropolyether silane is typically of the formula

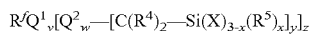

wherein:
R$^f$ is a polyfluoropolyether moiety;
Q$^1$ is a trivalent linking group;
each Q$^2$ is an independently selected organic divalent or trivalent linking group;
each R$^4$ is independently hydrogen or a C$_{1-4}$alkyl group;
each X is independently a hydrolysable or hydroxyl group;
R$^5$ is a C$_{1-8}$ alkyl or phenyl group;
v and w are independently 0 or 1, x is 0 or 1 or 2; y is 1 or 2; and z is 2, 3, or 4.

The polyfluoropolyether moiety R$^f$ can comprise perfluorinated repeating units selected from the group consisting of —(C$_n$F$_{2n}$O)—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6. In particular, n can be an integer from 1 to 4, more particularly from 1 to 3. For repeating units including Z the number of carbon atoms in sequence may be at most four, more particularly at most 3. Usually, n is 1 or 2 and Z is an —CF$_3$ group, more wherein z is 2, and R$^f$ is selected from the group consisting of —CF$_2$O(CF$_2$O)$_m$(C$_2$F$_4$O)$_p$CF$_2$—, —CF(CF$_3$)O(CF(CF$_3$)CF$_2$O)$_p$CF(CF$_3$)—, —CF$_2$O(C$_2$F$_4$O)$_p$CF$_2$—, —(CF$_2$)$_3$O(C$_4$F$_8$O)$_p$(CF$_2$)$_3$—, —CF(CF$_3$)—(OCF$_2$CF(CF$_3$)$_p$—O—C$_t$F$_{2t}$—O(CF(CF$_3$)CF$_2$O)$_p$CF(CF$_3$)—, wherein t is 2, 3 or 4 and wherein m is 1 to 50, and p is 3 to 40.

A cross-linking agent can be included. Typical cross-linking agents include tetramethoxysilane; tetraethoxysilane; tetrapropoxysilane; tetrabutoxysilane; methyl triethoxysilane; dimethyldiethoxysilane; octadecyltriethoxysilane; 3-glycidoxy-propyltrimethoxysilane; 3-glycidoxy-propyltriethoxysilane; 3-aminopropyl-trimethoxysilane; 3-aminopropyl-triethoxysilane; bis(3-trimethoxysilylpropyl) amine; 3-aminopropyl tri(methoxyethoxyethoxy) silane; N (2-aminoethyl)3-aminopropyltrimethoxysilane; bis(3-trimethoxysilylpropyl) ethylenediamine; 3-mercaptopropyltrimethoxysilane; 3-mercaptopropyltriethoxysilane; 3-trimethoxysilyl-propylmethacrylate; 3-triethoxysilypropylmethacrylate; bis(trimethoxysilyl) itaconate; allyltriethoxysilane; allyltrimethoxysilane; 3-(N-allylamino)propyltrimethoxysilane; vinyltrimethoxysilane; vinyltriethoxysilane; and mixtures thereof.

The component to be coated can be pre-treated before coating, typically by cleaning. Cleaning can be by way of a solvent, typically a hydrofluoroether, e.g. HFE72DE, or an azeotropic mixture of about 70% w/w trans-dichloroethylene; 30% w/w of a mixture of methyl and ethyl nonafluorobutyl and nonafluoroisobutyl ethers.

The above-described first acceptable coating is particularly useful for coating valves components, including one or more of valve stems, bottle emptiers, springs, and tanks, as well as canisters, such as metered dose inhalers, as described herein. This coating system can be used with any type of inhaler and any formulation described herein.

A second type of coating that can be used comprises a polyphenylsulphone. The polyphenylsulphone typically has the following chemical structure

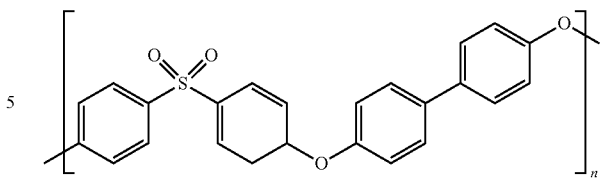

In this structure, n is the number of repeat units, which is typically sufficient to provide a weight average molecular weight from 10,000 to 80,000 daltons, for example, from 10,000 to 30,000 daltons. Other polymers, such as polyethersulphones, fluoropolymers such as PTFE, FEP, or PFA, can also be included. However, such other polymers are optional, and it is often advantageous to exclude them. Polyphenylsulphones can be difficult to apply by a solvent casting process. Thus, a special solvent system that is viable for use in a manufacturing setting can be employed for coating the polyphenylsulphones. On such solvent system employs a (1) first solvent that has a Hildebrand Solubility Parameter of at least 20.5 MPa$^{0.5}$ and at most 25 MPa$^{0.5}$, such as from 21 MPa$^{0.5}$ to 23.5 MPa$^{0.5}$; and (2) at least 20% by volume, often greater than 70% or greater than 80% by volume, of at least one 5-membered aliphatic, cyclic, or heterocyclic ketone based on the total volume of the solvent system. Optionally, a third component, namely a linear aliphatic ketone, can be included in amounts less than 5% by volume of the total volume of the solvent system.

Any first solvent that has a Hildebrand Solubility Parameter of at least 20.5 MPa$^{0.5}$ and at most 25 MPa$^{0.5}$ can be used, so long as the other components of the solvent system are as stated above. Some such first solvents are also -membered aliphatic, cyclic, or heterocyclic ketones, in which case the first solvent and the -membered aliphatic, cyclic, or heterocyclic ketone can be the same material. Other such solvents include acetonitrile.

The 5-membered aliphatic, cyclic, or heterocyclic ketone is typically a gamma lactone, such as gamma-butyrolactone, or a gamma lactam, such as a pyrolidone like 2-pyrrolidone, or an alkyl substituted 2-pyrrolidone like N-alkyl-2-pyrrolidones such as N-methyl-2-pyrrolidine (sometimes known by the acronym NMP). Other examples of 5-membered aliphatic, cyclic, or heterocyclic ketone that can be used include 2-methyl cyclopentanone, 2-ethyl cyclopentanone, and 2-[1-(5-methyl-2-furyl)butyl]cyclopentanone. Cyclopentanone is the most commonly used material. The optional linear aliphatic ketone can be any linear aliphatic ketone, and is typically acetone, although methyl ethyl ketone is also frequently employed.

The above-described second acceptable coating can be used on any type of inhaler, but is particularly useful for components of metered dose inhalers.

A third acceptable coating can be used to lower the surface energy of any component of an inhaler, such as a metered dose inhaler, but is particularly useful for valve stems, particularly those made of acetal polymer, as well as for stainless steel or aluminum components, particularly those used in canisters.

Such a coating can be formed on a component of an inhaler by the following process:
a) forming a non-metal coating on at least a portion of a surface of the medicinal inhalation device or a component of a medicinal inhalation device, respectively, said coating having at least one functional group;

b) applying to at least a portion of a surface of the non-metal coating a composition comprising an at least partially fluorinated compound comprising at least one functional group; and
c) allowing at least one functional group of the at least partially fluorinated compound to react with at least one functional group of the non-metal coating to form a covalent bond.

The at least one functional group of the non-metal coating is typically a hydroxyl group or silanol group. In most cases, the non-metal coating has a plurality of functional groups, particularly silanol groups, and can be formed, for example by plasma coating an organosilicone with silanol groups on the inhaler or one or more inhaler components. Typical organosilicon compounds include trimethylsilane, triethylsilane, trimethoxysilane, triethoxysilane, tetramethylsilane, tetraethylsilane, tetramethoxysilane, tetraethoxysilane, hexamethylcyclotrisiloxane, tetramethylcyclotetrasiloxane, tetraethylcyclotetrasiloxane, octamethylcyclotetrasiloxane, hexamethyldisiloxane, bistrimethylsilylmethane, and mixtures thereof. Most commonly, one or more of trimethylsilane, triethylsilane, tetramethylsilane, tetraethylsilane, bistrimethylsilylmethane are employed, with tetramethylsilane being most common. In addition to the organosilicon, the plasma can contain one or more of oxygen, a silicon hydride, particularly silicon tetrahydride, disilane, or a mixture thereof, or both. After deposition, the non-metal coating can be a diamond like glass or carbon like glass containing, on a hydrogen free basis, at 20 atomic percent or more of carbon and 30 atomic percent of more of silicon and oxygen combined.

The non-metal coating is often exposed to an oxygen plasma or corona treatment before applying the partially fluorinated compound. Most typically, an oxygen plasma treatment under ion bombardment conditions is employed.

The at least partially fluorinated compound often contains one or more hydrolysable groups, such as oxyalkly silanes, typically ethyoxy or methoxy silanes. A polyfluoropolyether segment, which in particular cases is a perfluorinated polyfluoroether, is typically used. Poly(perfluoroethylene) glycol is most common. Thus, the at least partially fluorinated compound can include a polyfluropolyether linked to one or more functional silanes by way of, for example, a carbon-silicon, nitrogen-silicon, or sulfer-silicon.

Examples of at least partially fluorinated compounds that can be used include those having the following formula:

wherein:
$R_f$ is a monovalent or multivalent polyfluoropolyether segment;
Q is an organic divalent or trivalent linking group;
each R is independently hydrogen or a $C_{1-4}$ alkyl group;
each Y is independently a hydrolysable group;
$R^{1a}$ is a $C_{1-8}$ alkyl or phenyl group;
x is 0 or 1 or 2;
y is 1 or 2; and
z is 1, 2, 3, or 4.

Typically, $R_f$, comprises perfluorinated repeating units selected from the group consisting of —$(C_nF_{2n}O)$—, —(CF(Z)O)—, —(CF(Z)$C_nF_{2n}O$)—, —($C_nF_{2n}$CF(Z)O)—, —(CF$_2$CF(Z)O)—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6. Particular examples of this compound are those where z is 1, $R_f$ is selected from the group consisting of $C_3F_7O(CF(CF_3)CF_2O)_pCF(CF_3)$—, $CF_3O(C_2F_4O)_pCF_2$—, $C_3F_7O(CF(CF_3)CF_2O)_pCF_2CF_2$—, $C_3F_7O(CF_2CF_2CF_2O)_pCF_2CF_2$—, $C_3F_7O(CF_2CF_2CF_2O)_pCF(CF_3)$— and $CF_3O(CF_2CF(CF_3)O)_p(CF_2O)X$—, wherein X is $CF_2$—, $C_2F_4$—, $C_3F_6$—, $C_4F_8$— and wherein the average value of p is 3 to 50. Other particular examples include those wherein z is 2, $R_f$ is selected from the group consisting of —$CF_2O(CF_2O)_p(C_2F_4O)_pCF_2$—, —$CF(CF_3)O(CF(CF_3)CF_2O)_pCF(CF_3)$—, —$CF_2O(C_2F_4O)_pCF_2$—, —$(CF_2)_3O(C_4FO)_p(CF_2)_3$—, —$CF(CF_3)$—$(OCF_2CF(CF_3))_pO$—$C_tF_{2t}$—$O(CF(CF_3)CF_2O)_pCF(CF_3)$—, wherein t is 2, 3 or 4 and wherein m is 1 to 50, and p is 3 to 40. Most commonly $R_f$ is one of —$CF_2O(CF_2O)_m(C_2F_4O)_pCF_2$—, —$CF_2O(C_2F_4O)_pCF_2$—, and —$CF(CF_3)$—$(OCF_2CF(CF_3))_pO$—$(C_tF_{2t})$—$O(CF(CF_3)CF_2O)_pCF(CF_3)$—, t is 2,3, or 4, and the average value of m+p or p+p or p is from about 4 to about 24. Q is commonly selected from the group consisting of —C(O)N(R)—$(CH_2)_k$—, —S(O)$_2$N(R)—$(CH_2)_k$—, —$(CH_2)_k$—, —$CH_2O$—$(CH_2)_k$—, —C(O)S—$(CH_2)_k$—, —$CH_2OC(O)N(R)$—$(CH_2)_k$—, and

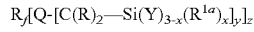

when R is hydrogen or $C_{1-4}$ alkyl, and k is 2 to about 25. In other common cases, Q is selected from the group consisting of —C(O)N(R)(CH$_2$)$_2$—, —OC(O)N(R)(CH$_2$)$_2$—, —CH$_2$O(CH$_2$)$_2$—, or —CH$_2$—OC(O)N(R)—(CH$_2$)$_2$—, R is hydrogen or $C_{1-4}$ alkyl, and y is 1.

Upon applying appropriate at least partially fluorinated compounds to the non-metallic coating, at least one covalent bond can form between the two, thereby completing the coating.

Yet another suitable coating is fluorinated ethylene propylene copolymer, sometimes known as FEP.

FEP coatings are particularly useful for coating one or more internal surfaces of a canister.

List of Exemplary Embodiments

The following embodiments are meant to be illustrative, and are not intended to be limiting unless otherwise specified.

1. A metered dose inhaler equipped with a metering valve and having an aerosol canister containing a pharmaceutical composition comprising,
propellant;
ethanol;
citric acid; and
tiotropium or a pharmaceutically acceptable salt or solvate thereof dissolved in the composition;
wherein the aerosol canister has an internal surface that is a non-metal material that is in contact with the pharmaceutical composition.

2. The metered dose inhaler of embodiment 1, wherein the pharmaceutical composition comprising tiotropium or a pharmaceutically acceptable salt or solvate thereof is tiotropium bromide.

3. The metered dose inhaler of any previous embodiment, wherein the propellant comprises 1,1-difluoroethane, 1,1,1,2-tetrafluoroethane, 1,1,1,2,3,3,3-heptafluoropropane, or combinations thereof.

4. The metered dose inhaler of any previous embodiment, wherein the propellant consists essentially of 1,1,1,2-tetrafluoroethane.
5. The metered dose inhaler of any one of embodiment 1-3, wherein the propellant consists essentially of 1,1-difluoroethane.
6. The metered dose inhaler of any previous embodiment, wherein the concentration of the tiotropium is between about 0.07 mg/mL and 0.15 mg/mL.
7. The metered dose inhaler of any previous embodiment, wherein the concentration of the tiotropium is between about 0.09 mg/mL and 0.13 mg/mL.
8. The metered dose inhaler of any previous embodiment, wherein the concentration of the tiotropium is between 0.005 wt. % and 0.015 wt. %
9. The metered dose inhaler of any previous embodiment, wherein the concentration of the citric acid is between about 0.02 wt. % and about 0.15 wt. %.
10. The metered dose inhaler of any previous embodiment, wherein the concentration of the citric acid is about 0.04 wt. %.
11. The metered dose inhaler of any previous embodiment, wherein in the concentration of the ethanol is no greater than about 20 wt. %.
12. The metered dose inhaler of any previous embodiment, wherein the concentration of the ethanol is between about 10 wt. % and 20 wt. %.
13. The metered dose inhaler of any previous embodiment, wherein in the concentration of the ethanol is about 15 wt. %.
14. The metered dose inhaler of any previous embodiment, wherein a metered dose is of between 3 micrograms and 6 micrograms per actuation.
15. The metered dose inhaler of any previous embodiment, wherein a metered dose is about 5 mcg per actuation.
16. The metered dose inhaler of any previous embodiment, wherein the non-metal material comprises a silane primer composition having two or more reactive silane groups separated by an organic linker group disposed thereon, wherein the silane primer composition has a coating composition comprising an at least partially fluorinated compound disposed thereon.
17. The metered dose inhaler of any previous embodiment, wherein the non-metal material comprises a polyfluoropolyether silane.
18. The metered dose inhaler of any previous embodiment, wherein the non-metal material comprises a fluorinated ethylene propylene (FEP) copolymer.
19. The metered dose inhaler of any previous embodiment, wherein the non-metal material comprises a polyphenylsulphone.
20. The metered dose inhaler of any previous embodiment, wherein the non-metal material comprises a diamond like glass or carbon like glass.
21. The metered dose inhaler of any previous embodiment, wherein the composition loses less than 5 wt. % of the tiotropium content after six months of storage inside an aerosol canister at a temperature of 25° C. and a relative humidity of 60%.
22. The metered dose inhaler of any previous embodiment wherein the metering valve is at least partially coated on its interior surface with a non-metal material.
23. The metered dose inhaler of embodiment 22, wherein the non-metal material comprises the material of any one of embodiment 16 to 20.
24. A method of making a metered dose inhaler of any previous embodiment, comprising admixing anhydrous tiotropium bromide, anhydrous ethanol, anhydrous citric acid, and anhydrous propellant.
25. A method of making a metered dose inhaler of any previous embodiment comprising sealing, under anhydrous conditions, an aerosol canister containing the pharmaceutical composition of any previous embodiment.
26. The method of embodiment 25, wherein at least a part of the pharmaceutical composition of any of embodiment 1 to 15 is cold-filled into the canister.
27. The method of embodiment 25, wherein at least a part of the pharmaceutical composition of any of embodiment 1 to 15 is filled into the canister under the application of pressure greater than atmospheric pressure.
28. The metered dose inhaler of any previous embodiment comprising an actuator with a nozzle orifice diameter of 0.2 mm to 0.65 mm.
29. The metered dose inhaler of any previous embodiment comprising an actuator with a nozzle orifice diameter of 0.2 mm to 0.3 mm.
30. The metered dose inhaler of embodiment 29 comprising an actuator with a nozzle orifice diameter of 0.25 mm.
31. The metered dose inhaler of embodiment 29 comprising an actuator with a nozzle orifice diameter of 0.3 mm.

EXAMPLES

Metered dose inhalers (MDIs) were prepared using deep drawn aluminum canisters (3M Corporation, Cltheroe, UK), 50 microliter Bespak PBT (polybutylene terephthalate) valves (BK0514719, Bespak Europe Ltd, Bergen Way, King's Lynn, Norfolk, PE30 2JJ) fitted with EPDM (ethylene-propylene diene terpolymer elastomer) diaphragm seals, and an Mk6 P&B actuator. The internal surface of each canister was coated with FEP (fluorinated ethylene propylene copolymer). The canisters were cold filled with the formulation shown in Table 1. The bulk formulation for cold filling individual canisters can be prepared by first admixing citric acid and the ethanol, and then adding the tiotropium bromide to the citric acid and ethanol mixture. HFA-134a propellant was then added to a separate batching vessel, and the mixture of tiotropium bromide, citric acid, and ethanol was then added be to the HFA-134a. The formulation was mixed at −50° C. The metered dose inhalers made according to Table 1 were designed to deliver 5 micrograms of Tiotropium (free base) per actuation.

FIG. 1 is a plot which demonstrates the consistency of manufacturing compositions with the desired concentration of tiotropium. FIG. 2 is a plot which demonstrates the consistency of manufacturing compositions with the desired citric acid concentration. FIG. 3 is a plot which demonstrates the consistency of manufacturing compositions with the desired ethanol concentration. FIG. 6 shows the mean stability of example compositions with respect to tiotropium content wherein the containers were stored either valve up (VU) or valve down (VD).

TABLE 1

| Formulation Composition | Hardware |
|---|---|
| Tiotropium Bromide 0.1204 mg/ml<br>Citric Acid 0.04 wt. %<br>Ethanol 15 wt. %<br>p134a to 100 wt % | FEP can<br>Bespak 50 mcl PBT Valve<br>Mk6 P&B actuator (primary) |

Next Generation Impactor (NGI) Studies

Figure 4:
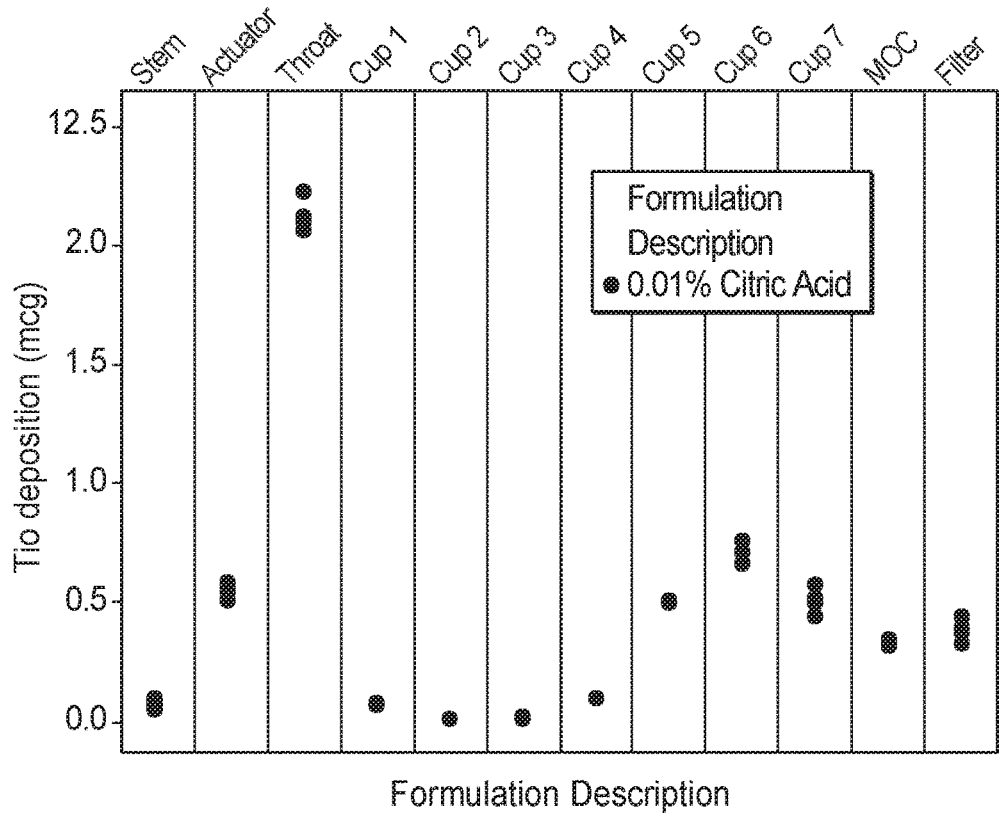
FIG. 4 is a plot of the tiotropium Aerodynamic Particle Size Distribution (APSD) for an example formulation.

The aerodynamic particle size distribution emitted from each MDI was evaluated using a Next Generation Impactor Instrument (MSP Corporation, Shoreview, MN). For each test, an MDI was attached to the throat component (Emmace anatomical throat, Emmace Consulting, Lund, Sweden) of the NGI instrument and actuated 6 times into the instrument. Prior to each actuation the MDI was vigorously shaken. Immediately prior to attachment, the MDI was primed by actuating 4 times. Prior to each priming shot the MDI was vigorously shaken. The flow rate through the instrument during testing was regulated at 30 L/minute. The test sample (tiotropium bromide) deposited on the valve stem, actuator, throat assembly (Emmace medium anatomical throat), individual uncoated collection cups 1-7, micro-orifice collector (MOC), and final filter component was collected by rinsing each individual component with a known volume of collection solvent. The recovered samples were then analyzed for sample content using an HPLC assay with reference to a known standard. The results of NGI studies are presented in FIG. 4 for the amount of tiotropium recovered from the valve stem, actuator, and each stage of the NGI instrument (throat assembly, cups 1 to 7, MOC, filter).

Delivered Dose Studies

Figure 5:
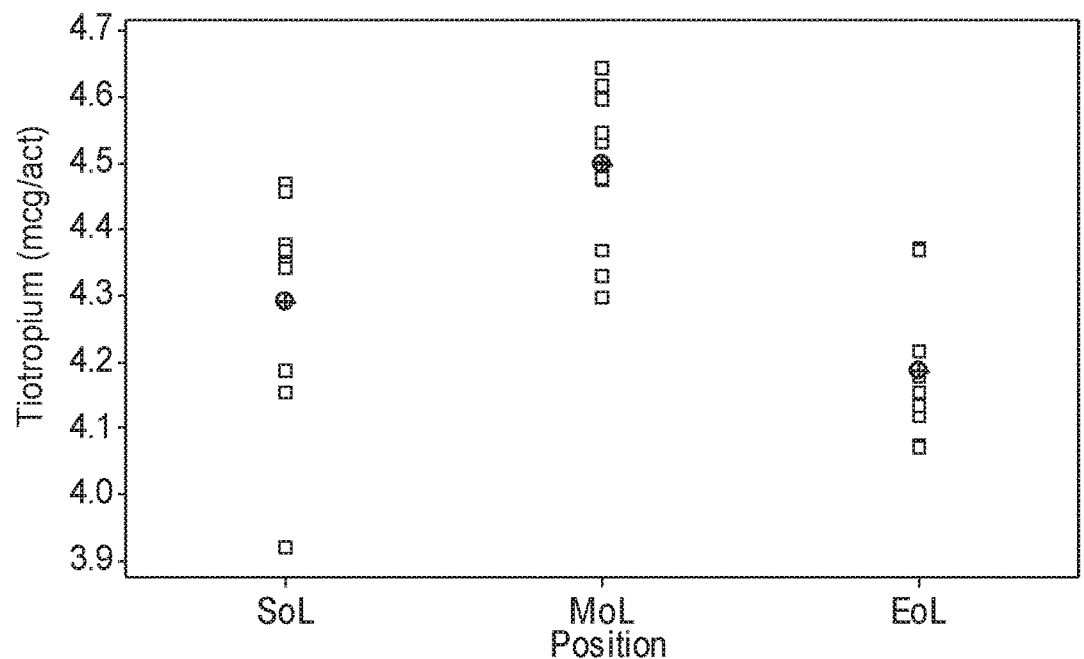
FIG. 5 is a plot of the tiotropium Uniformity of Delivered Dose (UoDD) for an example formulation.
Figure 6:
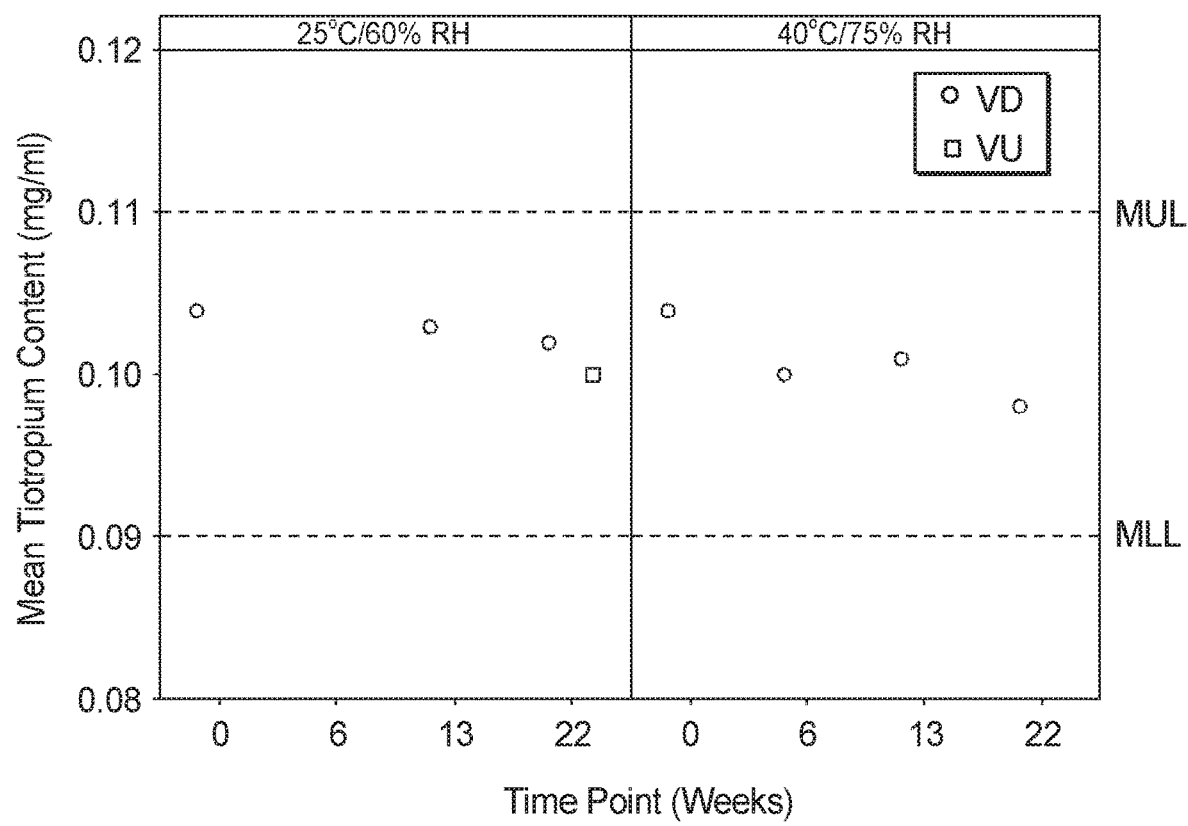
FIG. 6 is a plot of tiotropium stability for an example formulation.
Figure 7:
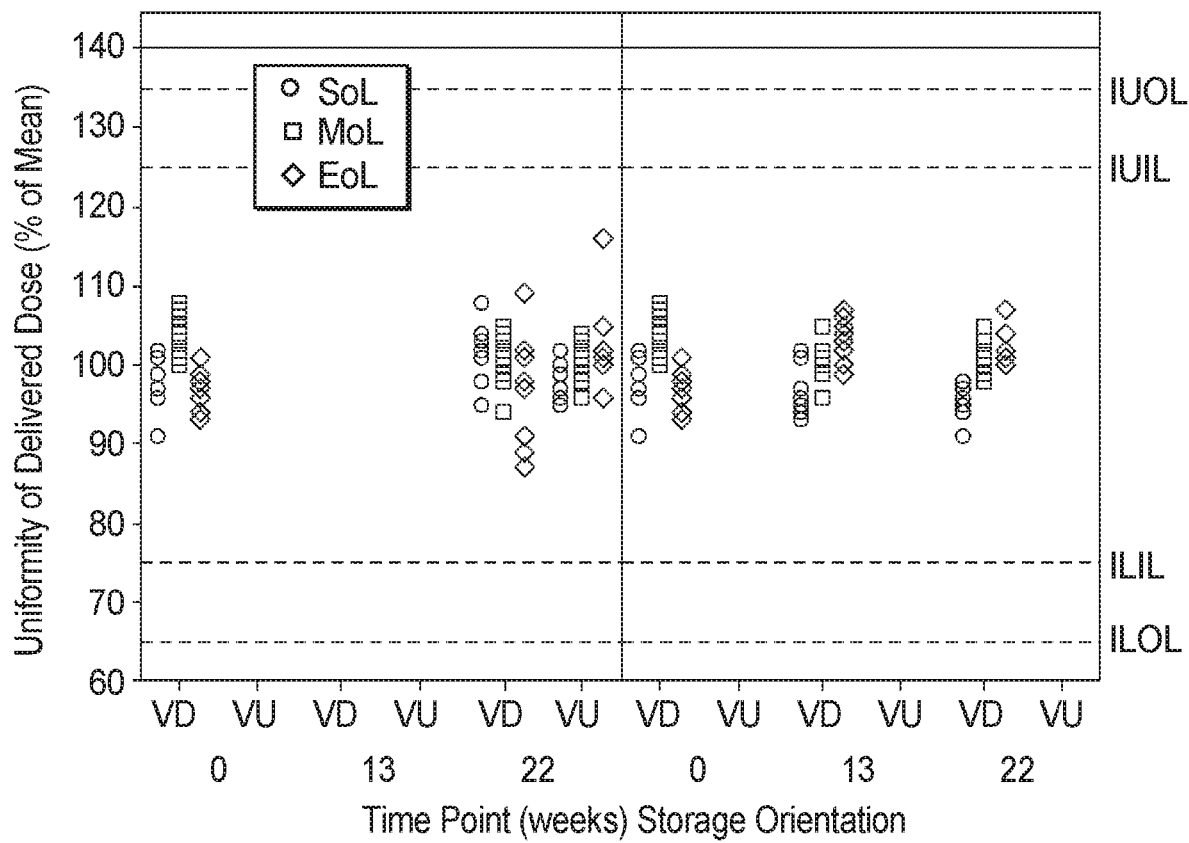
FIG. 7 is a plot of the tiotropium UoDD over time for an example formulation.

The start of unit life delivered dose was determined using standard unit spray collection apparatus (USCA) fitted with a filter. For each determination, an MDI was attached to the USCA using a coupler and actuated a single time. Immediately prior to attachment, the MDI was shaken. Prior to collection of the test sample, the MDI was primed by actuating four times. Prior to each priming shot the MDI was shaken. Start of life dose content uniformity for tiotropium bromide was 4.3 mcg/actuation as shown in FIG. 5. The uniformity of dose delivered remained constant on storage as shown in FIG. 7.

All references and publications cited herein are expressly incorporated herein by reference in their entirety into this disclosure.

Various features and aspects of the present disclosure are set forth in the following claims.

The invention claimed is:

1. A metered dose inhaler equipped with a metering valve and having an aerosol canister containing a pharmaceutical composition comprising:
propellant;
ethanol at a concentration of no greater than about 20 wt. %;
citric acid at a concentration of no greater than 0.07 wt. %; and
tiotropium or a pharmaceutically acceptable salt or solvate thereof dissolved in the composition;
wherein the aerosol canister has an internal surface that is a non-metal material that is in contact with the pharmaceutical composition,
wherein the pharmaceutical composition does not include water.

2. The metered dose inhaler of claim 1, wherein the pharmaceutical composition comprising tiotropium or a pharmaceutically acceptable salt or solvate thereof is tiotropium bromide.

3. The metered dose inhaler of claim 1, wherein the propellant comprises 1,1-difluoroethane, 1,1,1,2-tetrafluoroethane, 1,1,1,2,3,3,3-heptafluoropropane, or combinations thereof.

4. The metered dose inhaler of claim 1, wherein the propellant consists essentially of 1,1,1,2-tetrafluoroethane.

5. The metered dose inhaler of claim 1, wherein the concentration of the tiotropium is between about 0.07 mg/mL and 0.15 mg/mL.

6. The metered dose inhaler of claim 1, wherein the concentration of the tiotropium is between about 0.09 mg/mL and 0.13 mg/mL.

7. The metered dose inhaler of claim 1, wherein the concentration of the citric acid is between about 0.02 wt. % and 0.06 wt %.

8. The metered dose inhaler of claim 1, wherein the concentration of the citric acid is about 0.04 wt. %.

9. The metered dose inhaler of claim 1, wherein in the concentration of the ethanol is about 15 wt. %.

10. The metered dose inhaler of claim 1, wherein a metered dose is of between 3 micrograms and 6 micrograms per actuation.

11. The metered dose inhaler of claim 1, wherein the non-metal material comprises a silane primer composition having two or more reactive silane groups separated by an organic linker group disposed thereon, wherein the silane primer composition has a coating composition comprising an at least partially fluorinated compound disposed thereon.

12. The metered dose inhaler of claim 1, wherein the non-metal material comprises a polyfluoropolyether silane.

13. The metered dose inhaler of claim 1, wherein the non-metal material comprises a fluorinated ethylene propylene (FEP) copolymer.

14. The metered dose inhaler of claim 1, wherein the propellant consists essentially of 1,1-difluoroethane.

15. The metered dose inhaler of claim 1, wherein the non-metal material comprises a polyphenylsulphone.

16. The metered dose inhaler of claim 1, wherein the composition loses less than 5 wt. % of the tiotropium content after six months of storage inside an aerosol canister at a temperature of 25° C. and a relative humidity of 60%.

17. The metered dose inhaler of claim 1 wherein the metering valve is at least partially coated on its interior surface with a non-metal material.

18. The metered dose inhaler of claim 17, wherein the non-metal material comprises a silane primer composition having two or more reactive silane groups separated by an organic linker group disposed thereon, wherein the silane primer composition has a coating composition comprising an at least partially fluorinated compound disposed thereon.

19. A metered dose inhaler equipped with a metering valve and having an aerosol canister containing a pharmaceutical composition consisting of:
propellant;
ethanol at a concentration of no greater than about 20 wt. %;
citric acid at a concentration of no greater than 0.07 wt. %; and
tiotropium or a pharmaceutically acceptable salt or solvate thereof dissolved in the composition;

wherein the aerosol canister has an internal surface that is a non-metal material that is in contact with the pharmaceutical composition.

* * * * *